United States Patent [19]

Harvey

[11] Patent Number: 5,279,281
[45] Date of Patent: Jan. 18, 1994

[54] SINGLE-HANDED FIBRE-OPTIC FLEXIBLE LARYNGOSCOPE

[76] Inventor: James C. Harvey, Rte. 3, Box 288T, Sherwood, Oreg. 97140

[21] Appl. No.: 583,223

[22] Filed: Sep. 14, 1990

[51] Int. Cl.⁵ .............................................. A61B 1/06
[52] U.S. Cl. .................................. 128/4; 128/11
[58] Field of Search .................... 128/10, 11, 15, 16, 128/4, 6

[56] References Cited

U.S. PATENT DOCUMENTS

| | | | |
|---|---|---|---|
| 3,913,568 | 10/1975 | Carpenter | 128/11 |
| 3,994,557 | 11/1976 | Hopkins | 128/4 |
| 4,086,919 | 5/1978 | Bullard | |
| 4,141,362 | 2/1979 | Wurster | |
| 4,254,762 | 3/1981 | Yoon | |
| 4,337,761 | 7/1982 | Upsher | 128/11 |
| 4,360,008 | 11/1982 | Corazzelli, Jr. | 128/11 |
| 4,384,570 | 5/1983 | Roberts | |
| 4,390,012 | 6/1983 | Mizumoto | |
| 4,392,485 | 7/1983 | Hiltebrandt | 128/6 |
| 4,419,987 | 12/1983 | Ogiu | |
| 4,422,457 | 12/1983 | Hattori | 128/6 |
| 4,517,963 | 5/1985 | Michel | 128/6 |
| 4,580,551 | 4/1986 | Siegmund et al. | |
| 4,592,343 | 6/1986 | Upsher | 128/11 |
| 4,745,908 | 5/1988 | Wardle | |
| 4,753,222 | 6/1988 | Morishita | |
| 4,762,119 | 8/1988 | Allred, III et al. | |
| 4,773,395 | 9/1988 | Suzuki et al. | |
| 4,778,967 | 12/1988 | Ueda | |
| 4,805,595 | 2/1989 | Kanbara | |
| 4,838,245 | 6/1989 | Storz | 128/6 |
| 4,901,708 | 2/1990 | Lee | 128/11 |
| 4,905,669 | 3/1990 | Bullard et al. | 128/11 |
| 4,947,829 | 8/1990 | Bullard | 128/11 |

FOREIGN PATENT DOCUMENTS

| | | | |
|---|---|---|---|
| 2728910 | 1/1978 | Fed. Rep. of Germany | |
| 564856 | 3/1976 | U.S.S.R. | 128/4 |

Primary Examiner—Ralph Lewis
Attorney, Agent, or Firm—Kolisch, Hartwell, Dickinson, McCormack & Heuser

[57] ABSTRACT

A flexible laryngoscope is intended for use with a light source which produces a light beam. The laryngoscope includes a body which has a fibre-optic bundle extending therefrom including a fibre-optic cable having a viewing end and a movable free end. An eyepiece is carried on the body and is optically connected to the viewing end of the fibre-optic bundle. Suitable optics are provided for directing a light beam from the light source to the fibre-optic cable. A directing mechanism is provided and positions the fibre-optic cable at a substantially 90° angle to the eyepiece as the cable extends outwardly from the laryngoscope body. A guide mechanism is provided for controlling the location of the free end of the fibre-optic cable.

5 Claims, 4 Drawing Sheets

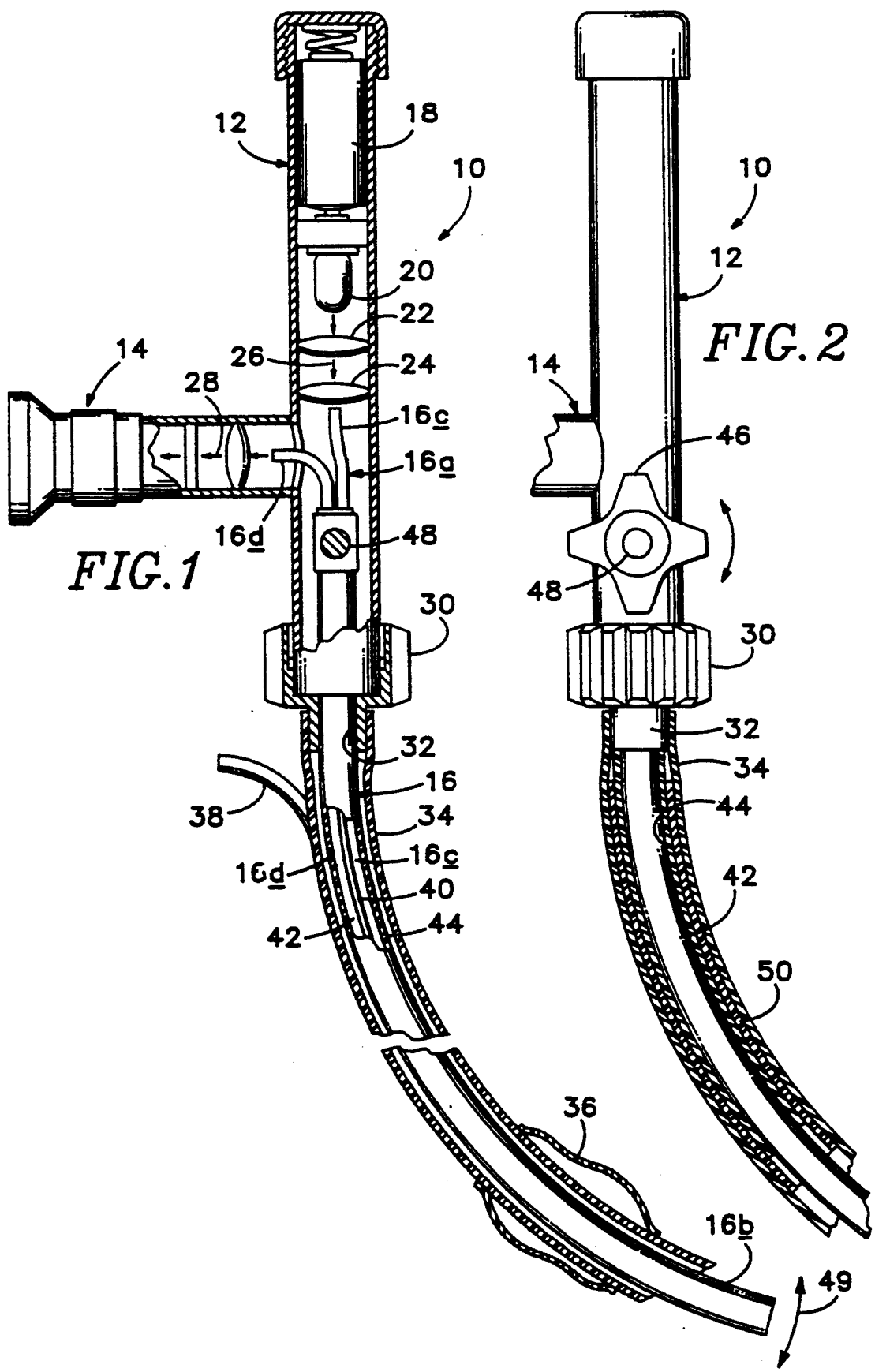

SINGLE-HANDED FIBRE-OPTIC FLEXIBLE LARYNGOSCOPE

BACKGROUND OF THE INVENTION

The present invention relates to laryngoscopes, and specifically to flexible laryngoscopes which may be used to insert an endotracheal tube into the trachea of a patient who is unconscious and who is to be connected to a breathing apparatus.

In the course of surgical procedures, wherein the patient is to be placed under general anesthetic and connected to an artificial breathing mechanism, an endotracheal tube must be inserted through the patient's mouth, into the throat and ultimately into the patient's trachea. The insertion of the endotracheal tube is complicated by the induction of anesthesia, which generally involves some type of injection to render the patient unconscious. In such a state, a patient, who is generally placed on his or her back, will be in a paralyzed condition which, among other things, allows the patient's tongue to fall rearward into the oral cavity, thereby blocking the throat and rendering insertion of the endotracheal tube through the vocal cords, voice box and into the trachea quite difficult.

One technique for inserting the endotracheal tube is to use a rigid laryngoscope, which allows the anesthesiologist to raise the person's tongue, thereby exposing the vocal cords and voice box, and then to insert the endotracheal tube through the vocal cords. In some instances, it may be necessary to use some type of optical instrument to view the vocal cords, thereby to successfully guide the free or distal end of the endotracheal tube into the patient's trachea. As may be readily concluded by those skilled in the art, the use of the rigid laryngoscope in conjunction with currently available flexible laryngoscopes is extremely difficult because more than two hands are required for successful manipulation of the instruments.

An object of the invention is to provide a flexible laryngoscope which allows for one-handed manipulation and placement of an endotracheal tube into the trachea of a patient.

Another object of invention is to provide a laryngoscope which allows viewing of the projected path of an associated endotracheal tube by an anesthesiologist.

A further object of the invention is to provide a flexible laryngoscope which directs a light source along the projected path of an endotracheal tube.

SUMMARY OF THE INVENTION

The flexible laryngoscope, or intubation device, of the invention is intended for use with a light source which produces a light beam. The laryngoscope includes a body which as a fibre-optic bundle extending therefrom which includes fibre-optic cables, one of which provides illumination to the subject area and the other of which provide for viewing of the subject area. The bundle may have a movable free end. An eyepiece is carried on the body and is optically connected to the viewing end of the fibre-optic bundle. Suitable optics are provided for directing a light beam from the light source to the illumination fibre-optic cable. A directing mechanism is provided and positions the fibre-optic cable at a substantially 90° angle to the eyepiece as the cable extends outwardly from the laryngoscope body.

A guide mechanism is provided for controlling the location of the free end of the fibre-optic cable.

These and other objects and advantages of the invention will become more fully apparent as the description which follows is read in conjunction with the drawings.

BRIEF DESCRIPTION OF THE DRAWINGS

FIG. 1 is a side view of a flexible laryngoscope constructed according to the invention, with portions broken away to show detail.

FIG. 2 is a side view of the laryngoscope of FIG. 1, having an auxiliary guide mechanism located about a fibre-optic bundle thereof.

DETAILED DESCRIPTION OF THE PREFERRED EMBODIMENTS

Figure 3:
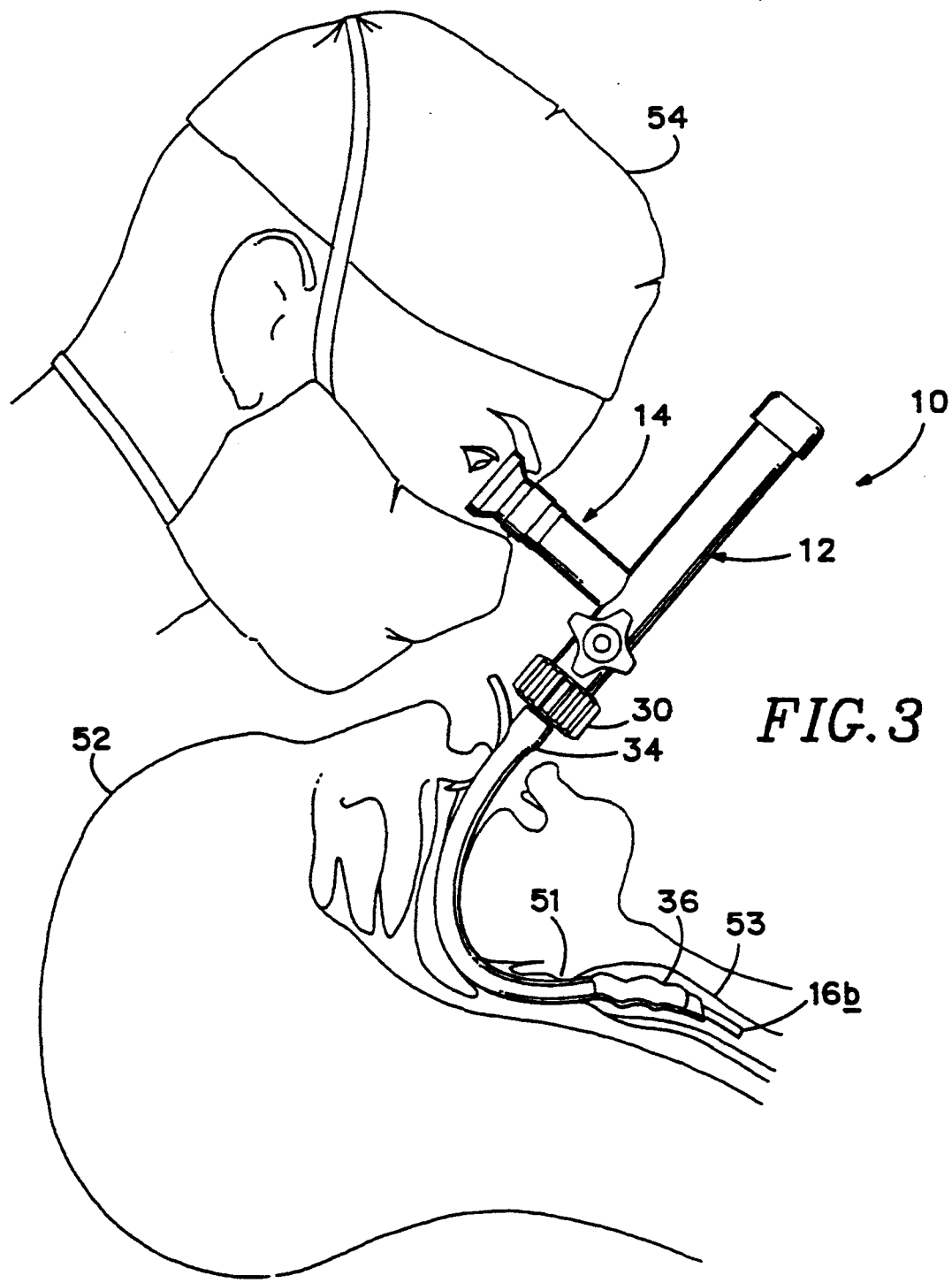
FIG. 3 is a side view of the laryngoscope of the invention depicted in an environmental setting.

Referring now to the drawings and initially to FIGS. 1, 2 and 3, a flexible laryngoscope constructed according to the invention is depicted generally at 10. Laryngoscope 10, also referred to herein as an intubation device, includes, in this embodiment, an elongate body 12 which has an eyepiece 14 carried thereon. A fibre-optic bundle 16 includes a viewing end 16a and a distal, free end 16b. Bundle 16 includes an illumination cable 16c and a viewing cable 16d.

Laryngoscope 10 further includes a light source, which in this embodiment is self contained in body 12 and includes a power supply or battery 18, and a light bulb 20. A pair of lenses 22, 24 is provided, and comprise what is referred to herein as optic means which direct a light beam 26 from the light source (battery 18 and bulb 20) to the viewing end 16a of fibre optic illumination cable 16c. An illuminating light beam 26 passes into end 16a of fibre-optic cable 16c, while a viewing light beam 28 returns along the length of fibre-optic viewing cable 16d is directed into eyepiece 14.

In this embodiment of the laryngoscope, a connector 30 is provided at the other end of the body 12 and includes a fitting 32 which receives a endotracheal tube 34 thereon. Fibre-optic bundle 16 extends through the central core of endotracheal tube 34. Bundle 16 is of sufficient length to extend beyond endotracheal tube 34 by an inch or two. The selection of the length of bundle 16 is important to allow free end 16b to serve as a guide for endotracheal tube 34 while simultaneously providing a view of the path of bundle 16 and endotracheal tube 34 to the anesthesiologist through eyepiece 14.

Tube 34 includes an inflatable balloon 36, located adjacent the distal end thereof. Balloon 36 is inflated by means of a tube 38 which extends along endotracheal tube 34. Once the endotracheal tube is in place, balloon 36 is inflated, thereby completely sealing the trachea of the patient providing for positive ventilation by means of conventional breathing apparatus (not shown) which is connected to endotracheal tube 34. Inflation of balloon 36 is generally accomplished by inserting the syringe into tube 38 and filling the balloon with air.

Fibre-optic bundle 16 may be provided with what is referred to herein as guide means. At least two forms of guide means are proposed. The first form includes the provision of a end-manipulable cable 40, which extends between the actual light-transmitting fibre-optic cable 42, located inside a sheath 44. Cable 42 and sheath 44 comprise fibre-optic bundle 16.

Cable 40 is connected to a knob 46, located on body 12. Cable 40 is connected to a shaft 48 which extends from knob 46 into body 12, such that cable 40 is extensible and retractable within sheath 44 upon twisting of knob 46. This allows movement of distal or free end 16b of fibre-optic bundle 16, as depicted by arrow 49. Such movement, provided by a drivable free end 16b, allows the anesthesiologist to precisely position the free end of the fibre-optic bundle as the anesthesiologist attempts to guide the bundle between the patient's vocal cords and into the trachea. Once the end of the fibre-optic bundle has been threaded between the vocal cords and into the trachea, the endotracheal tube may easily be inserted.

Another form of guide means is depicted in FIG. 2, and includes a stiff, yet malleable, sleeve 50 which prevents flexing of fibre-optic bundle 16 and the associated endotracheal tube. Sleeve 50 is positioned between endotracheal tube 34 and bundle 16. This form of guide means may also take the form of an internal stiffener (not shown) which is enclosed within fibre-optic bundle 16, or which may be placed over fibre-optic bundle 16 and inside an endotracheal tube. Sleeve 50 may be used with a laryngoscope having a fibre-optic bundle which is the same length as sleeve 50.

Referring now to FIG. 3, the laryngoscope is depicted in an environmental setting, with an endotracheal tube inserted down the throat 51 of a patient 52, and an anesthesiologist 54 viewing the placement of the free end 16b of the fibre-optic bundle, which is located in the patient's trachea 53, through the laryngoscope and fibre-optic cable.

Although the anesthesiologist hands are not depicted in FIG. 3, to avoid cluttering the drawing, it should be appreciated that the flexible laryngoscope of the invention may be easily manipulated with one hand, leaving the anesthesiologist a free hand with which to manipulate a rigid laryngoscope, which would be used to hold the patient's tongue out of the way. Although the patient is under close medical supervision, the patient will undoubtedly be under a high degree of stress, either from trauma or anxiety, and may be in shock. When possible, the patient will be provided with 100% oxygen for a few minutes before intubation to increase the patient's blood stream oxygen content. Additionally, the use of an optical device is necessitated by anatomical variations among patients, such as protruding teeth, a large tongue, a small mandible, or a high larynx, which makes the vocal cords difficult to view with a rigid laryngoscope. The patient may also be apneic unless the anesthesiologist has delivered a breath or two to the patient. In either situation, insertion of an endotracheal tube will be difficult. Because the patient is likely to be unconscious, and in a breathing impaired condition, the endotracheal tube must be quickly inserted. In such a condition, quickness is mandatory, while gentleness, and the traumatization of tissue must be secondary. The flexible laryngoscope of the invention provides for quick insertion of an endotracheal tube with a minimum of trauma to the patient's tissue.

To place endotracheal tube 34 in a patient's trachea, the anesthesiologist initially installs the endotracheal tube on flexible laryngoscope 10, fixing the upper end of the endotracheal tube to connector 30 and fitting 32. Connector 30 and fitting 32 are like those provided on conventional artificial breathing apparatus, which will provide positive ventilation to the patient during a surgical procedure.

The anesthesiologist inserts a rigid laryngoscope into the patient's mouth in order to raise the tongue, to provide a clear path to the patient's voice box. The patient's mouth is suctioned if necessary. Flexible laryngoscope 10, with endotracheal tube 34 installed thereon, is inserted into the patient's mouth such that the anesthesiologist can see the path taken by end 16b of fibre-optic bundle 16. End 16b is placed under direct vision in an area close to the patient's vocal cords. The anesthesiologist then views the oral cavity through device 10 to locate the patient's vocal cords. End 16b may be guided by both gross movements of laryngoscope 10 and by fine movements of end 16b, through the connection of cable 40 to knob 46, which is manipulable by the anesthesiologist. The anesthesiologist is able to hold laryngoscope 10 while simultaneously operating knob 46 with the same hand.

Once the anesthesiologist has located the patient's vocal cords, free end 16b of fibre-optic bundle 16 is gently inserted between the vocal cords. The anesthesiologist next directs free end 16b into the patient's trachea, again, looking for the proper path. Endotracheal tube 34 will be guided between the patient's vocal cords and into the trachea as the laryngoscope is further inserted into the patient's trachea.

Once the endotracheal tube is properly positioned, the flexible laryngoscope of the invention may be disconnected from the endotracheal tube and the laryngoscope and fibre-optic bundle withdrawn from the patient. The endotracheal tube may then be connected to a conventional breathing machine to ventilate the patient during surgical proceeding. Once the breathing machine is connected, balloon 36 is inflated by means of a hypodermic syringe and tube 38.

In the case where flexible laryngoscope 10 is not provided with cable 40 and the movable free end 16b of the fibre-optic bundle 16, a stiff, yet malleable sleeve 50 may be installed over endotracheal tube 34, as is depicted in FIG. 2. while this assembly does not allow the very fine adjustments of the laryngoscope having the controllable end, it is still possible to locate the patient's vocal cords and insert the fibre-optic bundle and endotracheal tube into the patient's trachea without traumatizing the tissue. In this embodiment, the insertion tube will be flush with the end of the endotracheal tube.

Regardless of the guide means provided, the provision of the eyepiece at a 90° angle to the fibre-optic bundle eliminates the need for the anesthesiologist to bend over the chest of the patient in order to view the laryngoscope. The difference in the location of the anesthesiologist may be visualized, with the use of FIG. 3, by imagining that the anesthesiologist is required to view the laryngoscope through the end of the laryngoscope containing the light source. Such an arrangement requires an extension of the anesthesiologist's body by 12-18 inches, which potentially places the anesthesiologist off-balance, in a somewhat precarious position. Changing the location of the eyepiece by 90° eliminates the problem.

Figure 5:
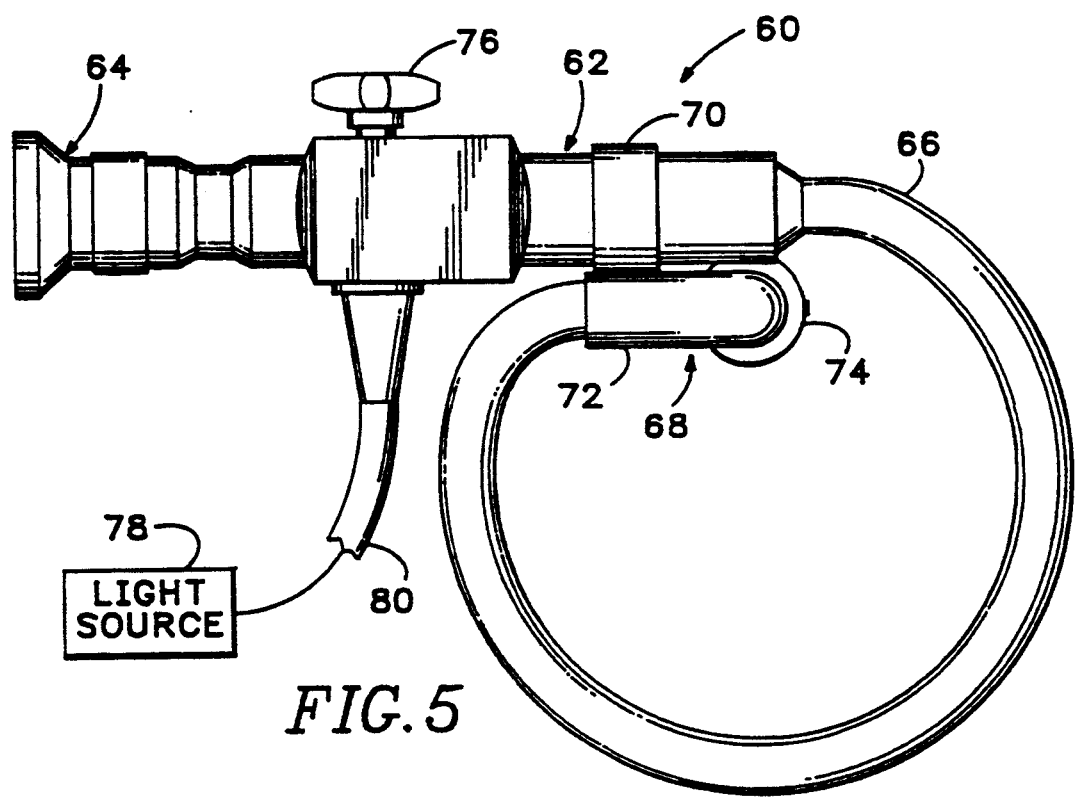
FIG. 5 is a top plan view of the first modified form of the invention depicted in FIG. 4.
Figure 4:
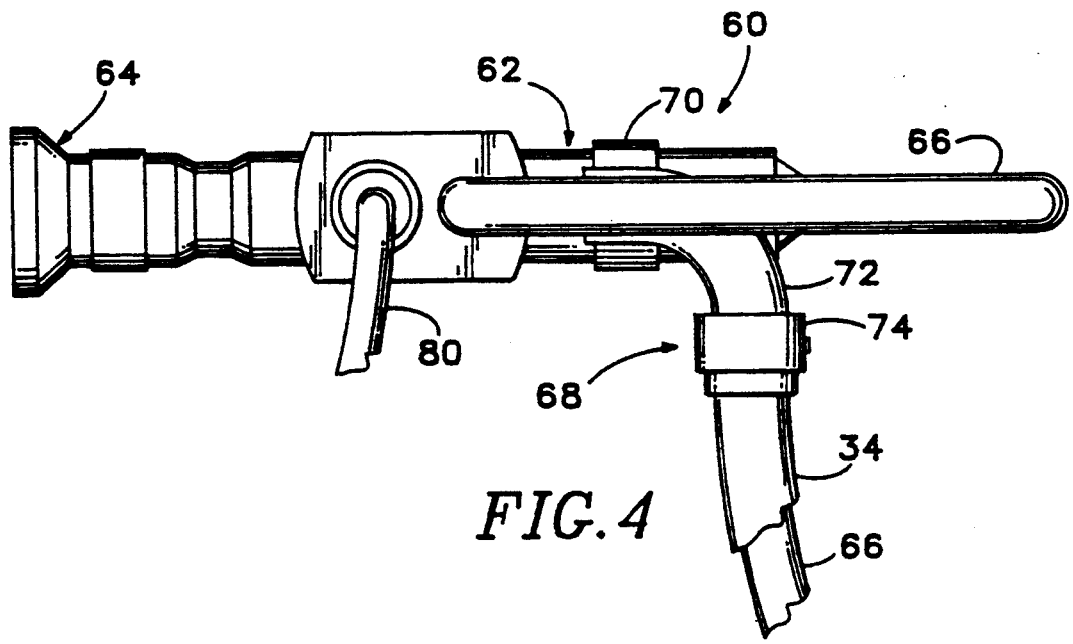
FIG. 4 is a side view of a first modified form of the invention.

Turning now to FIGS. 4 and 5, another embodiment of the flexible laryngoscope of the invention is depicted generally at 60. In this embodiment, a conventionally arranged flexible laryngoscope body 62 includes an eyepiece 64 at one end thereof and has a fibre-optic bundle 66 extending outwardly from the other end thereof, along the longitudinal axis of the body. Such a flexible laryngoscope is produced by Olympus or Ashai Pentax Companies and marketed under the designation flexible laryngoscope or bronchoscope.

In order to direct the fibre-optic bundle at a substantially 90° angle from the eyepiece, a directing means, shown generally at 68 is provided. Directing means, in this embodiment, includes a sleeve 70 which is clearance fittable over the other end of body 62 and includes what is referred to herein as right-angle means 72 secured to the sleeve. Right-angle means, or 90° elbow, 72 includes a connector 74 which receives endotracheal tube 34. Elbow 72 may be somewhat flexible to allow relative movement between body 62 and connector 74, which provides relative angular movement between body 62 and the endotracheal tube. Flexible laryngoscope 60 includes a knob 76, which is used to manipulate a cable extending along fibre-optic 66, to manipulate the end thereof. Alternately, a stiff sleeve may be provided over endotracheal tube 34, or a stiff wire may be inserted into the endotracheal tube with the fibre-optic bundle.

In this embodiment of the laryngoscope, a light source 78 is provided and remotely located from laryngoscope 60. The light source is connected to the laryngoscope by means of a fibre-optic connector 80 which is connected to optic means (not shown) located inside of body 62.

This embodiment is used similarly to that described above. The embodiment has the advantage of being used with a conventional flexible laryngoscope while providing the advantages of the first embodiment described herein.

Figure 7:
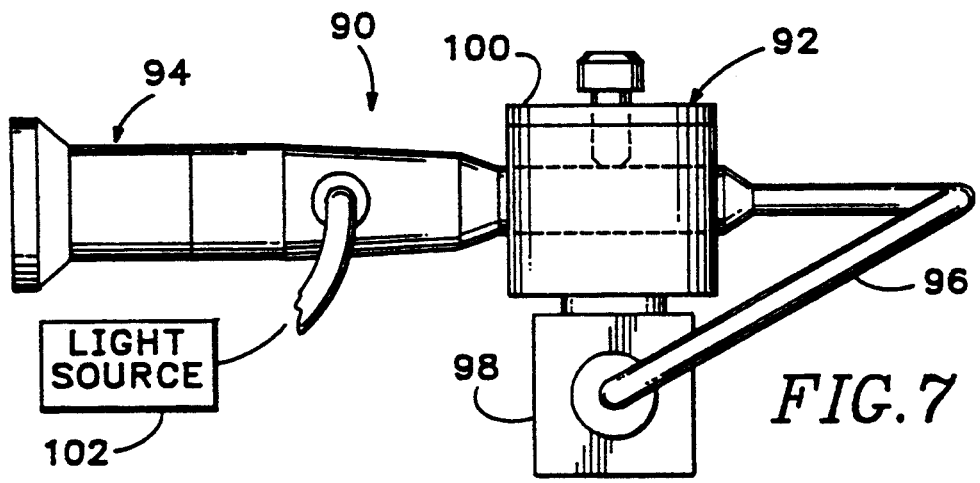
FIG. 7 is a top plan view of the laryngoscope of FIG. 6.
Figure 6:
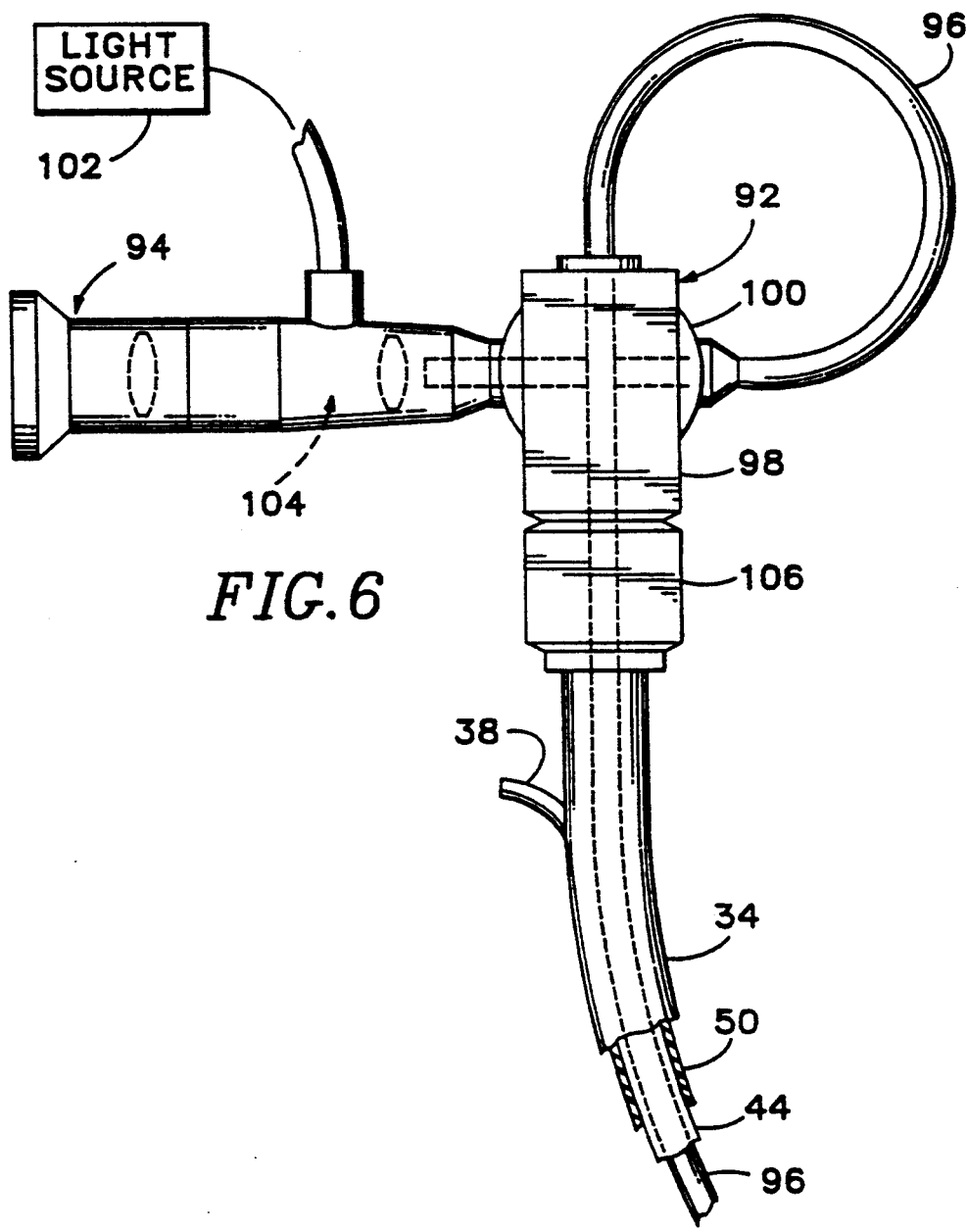
FIG. 6 is a side elevation of a second modified form of a flexible laryngoscope of the invention.

Referring now to FIGS. 6 and 7, a third embodiment of the laryngoscope is shown generally at 90. Flexible laryngoscope 90 is extremely compact and lightweight. It incorporates a conventional fibre-optic viewing device such as that manufactured by the Microvasive Company. While it does not incorporate the flexible, end-manipulable cable 40, it has other features which compensate for the lack of the drivable free end of the fibre-optic bundle.

A laryngoscope body 92 has an eyepiece 94 located thereon which is connected to a fibre-optic bundle 96. In this form of the invention, a guide means holder 98 and an eyepiece holder 100 are arranged to provide relative rotation between the eyepiece and the guide means. Laryngoscope body 92 and eyepiece 94 are received in eyepiece holder 100 while fibre-optic bundle 96 is trained between eyepiece holder 100 and guide means holder 98.

A light source 102 provides a light beam to optics 104 in the body/eyepiece which is transmitted through fibre-optic bundle 96. A connector 106 is provided to receive an endotracheal tube 34, which may be equipped with a stiff sleeve or stiff tubular member 50, to guide the endotracheal tube into proper position. The provision of the relative rotation means allows more freedom of movement for the anesthesiologist and less stress on the patient's tissue during intubation. This arrangement allows for maximum convenience for the anesthesiologist, who may adjust the relative position of the eyepiece and guide means to whatever position is most comfortable.

Although a preferred embodiment of the invention has been disclosed, it should be appreciated that variations and modifications may be made thereto without departing from the scope of the invention as defined in the appended claims.

What I claim is:

1. A flexible laryngoscope for use with a light source which produces a light beam comprising:
    an elongate laryngoscope body with a fibre-optic cable extending longitudinally outwardly from one end thereof, said cable having a viewing end attached to said body and a movable free end remote from the body;
    an eyepiece carried on the other end of said body optically connected to said cable for viewing its said viewing end;
    optic means joined to said body adjacent said cable's said viewing end for directing a light beam from the light source to said cable;
    directing means joined to said body including a sleeve which is clearance fittable over said one end of said body, and right-angle means secured to said sleeve insertably receiving said fibre-optic cable in a manner fixing the cable, at the location of said right-angle means, in a condition extending laterally outwardly at substantially a 90° angle relative to the long axis of the body, which axis substantially coincides with the viewing axis of said eyepiece, with said cable thus extending outwardly and freely away laterally relative to the body; and
    guide means mounted on said body and operatively connected to said cable for controlling the location of said cable's said free end.

2. The laryngoscope of claim 1, wherein said guide means includes an elongate stiff member disposed along and adjacent said fibre-optic cable.

3. A one-handed-operable intubation device for inserting an endotracheal tube into a trachea, for use with an endotracheal tube, comprising:
    a light source which produces a light beam;
    a flexible laryngoscope having a laryngoscope body, a fibre-optic cable extending from said body, said cable having a viewing end attached to said body and a movable free end remote from said body, optic means joined to said body adjacent said cable's said viewing end for directing the light beam from said source to said cable, and an eyepiece optically connected to said cable for viewing the cable's said viewing end;
    one-handed insertion means attached to said body, including:
    directing means joined to said body for positioning and fixing said fibre-optic cable in a condition with its long axis at a substantially 90° angle relative to the viewing axis of said eyepiece at a location where said cable extends outwardly and freely away from said body;
    guide means mounted on said body and operatively connected to said cable for controlling the location of said cable's free end, said guide means including an elongate stiff member disposed along and adjacent said cable; and
    connection means for releasably connecting an endotracheal tube to said one-handed insertion means adjacent said directing means.

4. A one-handed-operable intubation device for inserting a endotracheal tube into a trachea, for use with an endotracheal tube, comprising:

a light source which produces a light beam;

a laryngoscope having an elongate laryngoscope body with a fibre-optic cable extending longitudinally outwardly from one end thereof, said cable having a viewing end attached to said body and a movable free end remote from the body, optic means joined to said body adjacent said cable's said viewing end for directing a light beam from said source to said cable, and an eyepiece optically connected to said cable for viewing the cable's said viewing end;

one-handed insertion means attached to said body, including;

directing means joined to said body including a sleeve which is clearance fittable over said one end of said body, and right-angle means secured to said sleeve insertably receiving said fibre-optic cable in a manner fixing the cable, at the location of said right-angle means, in a condition extending laterally outwardly at substantially a 90° angle relative to the long axis of said body, which axis substantially coincides with the viewing axis of said eyepiece, with said cable thus extending outwardly and freely away laterally relative to the body;

guide means mounted on said body and operatively connected to said cable for controlling the location of said cable's said free end; and connection means for releasably connecting an endotracheal tube to said one-handed insertion means adjacent said directing means.

5. The intubation device of claim 4, wherein said body further includes a guide means holder for holding said guide means and an eyepiece holder for holding said eyepiece, and wherein said directing means further includes relative rotation means for accommodating relative rotation between said eyepiece holder and said guide means.

* * * * *